(12) United States Patent
Krapf et al.

(10) Patent No.: US 10,261,040 B2
(45) Date of Patent: Apr. 16, 2019

(54) MEASURING DEVICE, ESPECIALLY MOISTURE MEASURING DEVICE

(71) Applicant: Robert Bosch GmbH, Stuttgart (DE)

(72) Inventors: Reiner Krapf, Filderstadt (DE); Michael Frank, Bretten (DE); Wolfgang Baierl, Schorndorf (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 15/321,965

(22) PCT Filed: Jun. 17, 2015

(86) PCT No.: PCT/EP2015/063595
§ 371 (c)(1),
(2) Date: Dec. 23, 2016

(87) PCT Pub. No.: WO2015/197445
PCT Pub. Date: Dec. 30, 2015

(65) Prior Publication Data
US 2017/0138881 A1 May 18, 2017

(30) Foreign Application Priority Data
Jun. 25, 2014 (DE) .......... 10 2014 212 136

(51) Int. Cl.
*G01N 27/22* (2006.01)
*G01N 33/38* (2006.01)

(52) U.S. Cl.
CPC ......... *G01N 27/223* (2013.01); *G01N 33/383* (2013.01)

(58) Field of Classification Search
CPC .......... G01N 27/223; G01N 33/383

USPC ......... 324/640, 664, 694
See application file for complete search history.

(56) References Cited

U.S. PATENT DOCUMENTS

| | | | | |
|---|---|---|---|---|
| 4,724,381 A | * | 2/1988 | Crimmins | G01R 15/26 324/127 |
| 6,340,892 B1 | * | 1/2002 | Rynhart | G01N 27/048 324/640 |
| 7,038,470 B1 | * | 5/2006 | Johnson | G01N 27/226 250/390.05 |

(Continued)

FOREIGN PATENT DOCUMENTS

| | | |
|---|---|---|
| CN | 201269860 Y | 7/2009 |
| CN | 102885624 A | 1/2013 |

(Continued)

OTHER PUBLICATIONS

International Search Report corresponding to PCT Application No. PCT/EP2015/063595, dated Aug. 28, 2015 (German and English language document) (9 pages).

(Continued)

*Primary Examiner* — Farhana A Hoque
(74) *Attorney, Agent, or Firm* — Maginot, Moore & Beck LLP

(57) ABSTRACT

A measuring device includes an integrated sensor unit. The integrated sensor unit is configured to record at least one moisture characteristic value of at least one building material. The measuring device further includes a communication unit. The communication unit is configured to receive at least one signal from at least one external sensor unit.

10 Claims, 1 Drawing Sheet

(56) References Cited

U.S. PATENT DOCUMENTS

| | | | | |
|---|---|---|---|---|
| 7,126,486 B2* | 10/2006 | Kroll | ................... | E04B 1/70 |
| | | | | 340/604 |
| 2006/0117833 A1* | 6/2006 | Kanare | ................ | G01N 19/10 |
| | | | | 73/29.02 |
| 2013/0021034 A1* | 1/2013 | Heismann | .............. | A61B 5/742 |
| | | | | 324/318 |

FOREIGN PATENT DOCUMENTS

| | | |
|---|---|---|
| DE | 10 2012 208 050 A1 | 11/2013 |
| GB | 2 347 220 B | 8/2000 |

OTHER PUBLICATIONS

Jin, Xiaohua, et al., "Reflection and Transmission Properties of Embedded Dipoles and PIFAs inside Concrete at 915 MHz", Univ. of S. Carolina, 2009, 978-1-4244-3647-7/09, pp. 1-4.

\* cited by examiner

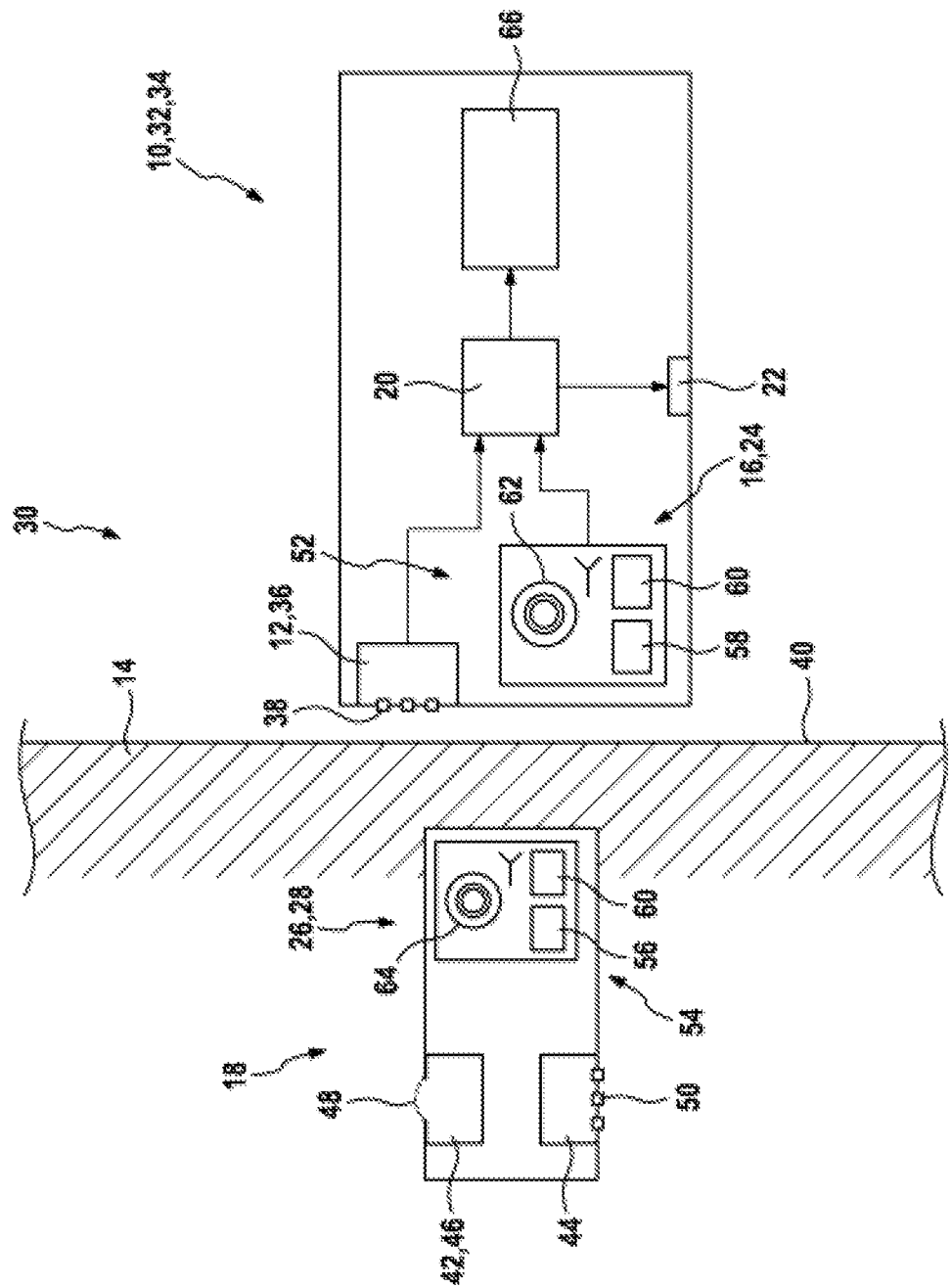

MEASURING DEVICE, ESPECIALLY MOISTURE MEASURING DEVICE

This application is a 35 U.S.C. § 371 National Stage Application of PCT/EP2015/063595, filed on Jun. 17, 2015, which claims the benefit of priority to Serial No. DE 10 2014 212 136.1, filed on Jun. 25, 2014 in Germany, the disclosures of which are incorporated herein by reference in their entirety.

BACKGROUND

A measuring device having an integrated sensor unit which is intended to determine an absolute and/or relative humidity of a solid, in particular a building material, has already been proposed.

SUMMARY

The disclosure is based on a measuring device, especially a moisture measuring device, having an integrated sensor unit which is intended to record at least one moisture characteristic value of at least one building material.

It is proposed that the measuring device comprises a communication unit which is intended at least to receive at least one signal from at least one external sensor unit.

In this context, a "measuring device" is supposed to be understood as meaning, in particular, a device which is in the form of a mobile apparatus, preferably a handheld apparatus, and is intended, in particular, to record and/or evaluate and/or store and/or output at least one measured value. In this context, a "sensor unit" is supposed to be understood as meaning, in particular, a unit which is intended to qualitatively record, in particular, physical and/or chemical properties and/or the material nature of its environment and/or to quantitatively record it/them as a measurement variable. "Intended" is supposed to be understood as meaning, in particular, specially programmed, designed and/or equipped.

The fact that an object is intended for a particular function is supposed to be understood as meaning, in particular, the fact that the object performs and/or carries out this particular function in at least one application and/or operating state. In this context, an "integrated sensor unit" is supposed to be understood as meaning, in particular, a sensor unit which is at least partially arranged inside a housing of the measuring device and/or is inseparably connected to further units of the measuring device, in particular to the communication unit. The integrated sensor unit is preferably in the form of a moisture sensor unit which is intended to record at least one moisture characteristic value of a building material, preferably in a non-destructive manner. In particular, the integrated sensor unit can record the at least one moisture characteristic value radiometrically and/or resistively and/or capacitively and/or using a microwave/radar method and/or using a one-sided access NMR method.

In this context, a "moisture characteristic value" is supposed to be understood as meaning, in particular, a characteristic value which contains at least one item of information relating to an absolute and/or relative moisture content of at least one building material, in particular. In this context, a "building material" is supposed to be understood as meaning, in particular, a solid, in particular in the form of a raw material and/or an auxiliary material and/or a semi-finished product which is intended to be used when constructing a structure and/or a building and/or a component. In this context, a "component" is supposed to be understood as meaning, in particular, an individual part, an element and/or a component from which a structure and/or a building is/are composed. A component is, in particular, a geometrically contiguous wall and/or floor surface and/or body having an at least substantially uniform structure and/or design. In this context, a "communication unit" is supposed to be understood as meaning, in particular, a unit which is intended to receive, in particular, at least one analog and/or digital signal from at least one external sensor unit in a wired and/or preferably wireless manner and/or to transmit at least one signal, in particular a control and/or parameterization signal, to the at least one external sensor unit. In this context, a "signal" is supposed to be understood as meaning, in particular, a measurable physical variable, in particular an electrical voltage and/or preferably an electrical and/or magnetic field, to which at least one item of information is assigned and/or on which at least one item of information is impressed.

In this context, an "external sensor unit" is supposed to be understood as meaning, in particular, a sensor unit which is intended to be operated separately from the measuring device. The at least one external sensor unit is preferably intended to record at least one characteristic value of the at least one building material directly inside the at least one building material. The at least one external sensor unit is preferably intended to transmit, in particular, at least one recorded characteristic value to the communication unit of the measuring device in a wired and/or preferably wireless manner.

The configuration according to the disclosure makes it possible to provide a measuring device of the generic type having advantageous operating properties. In particular, characteristic values from the integrated sensor unit and from at least one external sensor unit can be advantageously recorded in a parallel manner and/or with a time delay. This makes it possible to record and/or evaluate a multiplicity of different and/or preferably identical characteristic values in an advantageously simple and/or rapid manner.

It is also proposed that the at least one signal comprises at least one further moisture characteristic value of the at least one building material. The fact that the at least one signal "comprises" at least one further moisture characteristic value of the at least one building material is supposed to be understood as meaning, in particular, the fact that the at least one signal comprises useful data and/or at least one useful data packet which contain and/or contains at least one item of information relating to a moisture characteristic value which is preferably recorded by the at least one external sensor unit. Furthermore, the at least one signal may comprise management data and/or at least one management data packet which contain and/or contains, in particular, at least one item of control and/or log information. As a result, at least one further moisture characteristic value can be transmitted to the measuring device in an advantageously simple and/or secure and/or reliable manner.

It is also proposed that the communication unit is intended to wirelessly receive the at least one signal and/or to wirelessly transmit at least one signal. The phrase "wirelessly receive" is supposed to be understood as meaning, in particular, the fact that the communication unit is intended to receive the signal via an advantageously bodiless information carrier, for example via sound, light and/or preferably radio waves.

The communication unit is preferably in the form of an RFID communication unit (RFID=Radio Frequency Identification). This makes it possible to transmit the at least one signal from the at least one external sensor unit to the measuring device in an advantageously convenient manner.

Furthermore, the communication unit can advantageously be used simply to wirelessly transmit signals.

One preferred configuration of the disclosure proposes that the measuring device comprises a computing unit which is intended to offset the at least one moisture characteristic value against the at least one further moisture characteristic value. A "computing unit" is supposed to be understood as meaning, in particular, a unit which can be formed by an evaluation unit and/or a control unit, the computing unit being able to be formed both by a processor alone and, in particular, by a processor and further electronic components, for example a storage means. The fact that the at least one moisture characteristic value is "offset" against the at least one further moisture characteristic value is supposed to be understood as meaning, in particular, the fact that the at least one moisture value and the at least one further moisture characteristic value are included, in particular as parameters, in at least one mathematical and/or logical operation carried out by the computing unit. A result of the at least one mathematical and/or logical operation can be stored and/or buffered for further use, in particular, and/or can be output to a user. This makes it possible to advantageously evaluate the moisture characteristic values. In particular, the at least one moisture value and the at least one further moisture value can advantageously be related to one another.

It is also proposed that the computing unit is intended to determine at least one compensation characteristic variable from the at least one moisture characteristic value and the at least one further moisture characteristic value. In this context, a "compensation characteristic variable" is supposed to be understood as meaning, in particular, a characteristic variable which reflects at least one difference, in particular a difference caused by the measuring technique, between the at least one moisture characteristic value and the at least one further moisture characteristic value. In particular, a difference between the at least one moisture characteristic value and the at least one further moisture characteristic value can be at least substantially compensated for by applying the at least one compensation variable to the at least one moisture characteristic value.

As a result, simple and/or precise differences between the at least one moisture characteristic value and the at least one further moisture characteristic value, which occur, in particular, on account of differing measuring methods, can be advantageously at least largely corrected. In particular, measurement errors of the internal sensor unit can therefore be advantageously compensated for.

If the measuring device has at least one interface which is intended to transmit data to at least one external data processing unit, data recorded and/or generated and/or buffered by means of the measuring device can be advantageously easily retrieved from the measuring device, in particular for storage and/or further processing. In this context, an "interface" is supposed to be understood as meaning, in particular, a data interface which can be used to couple the measuring device to at least one external data processing unit in a wireless and/or wired manner. In this context, an "external data processing unit" is supposed to be understood as meaning, in particular, a unit which is independent of the measuring device and is intended, in particular, to acquire and/or store and/or preprocess and/or evaluate data.

The measuring device preferably comprises an energy transmitting unit which is intended to contactlessly supply energy to the at least one external sensor unit. In this context, an "energy transmitting unit" is supposed to be understood as meaning, in particular, a unit which is intended to transmit electrical energy, in particular, to the at least one external sensor unit using an inductive and/or electromagnetic method. The energy transmitting unit is preferably integrally formed with the communication unit. This makes it possible to supply the at least one external sensor unit with electrical energy in an advantageously simple manner. In particular, it is possible to dispense with an energy source inside the at least one external sensor unit, as a result of which a lifetime of the at least one external sensor unit can be advantageously extended.

The energy transmitting unit is preferably integrally formed with the communication unit. This means that the energy transmitting unit and the communication unit are formed by the same unit or the same subassembly. The energy transmitting unit is advantageously also used as a communication unit at the same time. This makes it possible to supply the at least one external sensor unit with electrical energy in an advantageously simple manner. In particular, it is possible to dispense with an energy source inside the at least one external sensor unit, as a result of which a lifetime of the at least one external sensor unit can be advantageously extended.

An external sensor unit for use with a measuring device with or without sensors is also proposed, the external sensor unit having at least one sensor which is intended to record a moisture characteristic value of at least one building material. In this case, the sensor may be a capacitive moisture sensor or else a watertight MEMS humidity sensor. In this case, the sensor of the external sensor unit is, in particular, a sensor which measures the air humidity and can measure the equilibrium moisture with the building material via a membrane. Alternatively or additionally, it is possible to use a moisture sensor which is in contact with the building material either capacitively or resistively via electrodes and therefore determines the local moisture.

The external sensor device in the form of a watertight module, in particular, can advantageously measure the temperature in the building material, which temperature can then be used to determine the dew point in the masonry. For this purpose, the external sensor device may additionally also have at least one temperature sensor.

The measurement data from the external sensor unit, for example temperature and moisture, can be advantageously read using a measuring device which is separate from the external sensor unit but is preferably supplied with energy by the latter.

The external sensor unit preferably comprises an energy provision unit which is intended to contactlessly supply energy to the at least one external sensor unit, in particular the sensors or sensor of the external sensor unit. In this context, an "energy provision unit" is supposed to be understood as meaning, in particular, a unit which is intended, in particular, to accept electrical energy by means of an inductive and/or electromagnetic method and to make it available to the components of the external sensor unit.

The energy provision unit may be, for example, an RFID tag or an inductive system, optionally with a transitional energy store, for example a rechargeable battery or a capacitor, and can receive energy from an external transmitter, for example the energy transmitting unit of the measuring device.

The external sensor unit also comprises a data communication unit, for example an RFID tag or a Bluetooth low-energy module, a ZigBee module or the like. A measured value store and/or a flow controller, in particular for the sensor, can be optionally, which is intended to forward data from the external sensor unit, for example a moisture characteristic value, to an assigned measuring device which is separate from the external sensor unit, however, in particular a handheld measuring device. The communication unit is preferably intended to communicate with the communication unit of the measuring device, in particular in a bidirectional manner.

The energy provision unit and the data communication unit of the external sensor device are preferably formed by the same component. This unit (for example an RFID tag) supplies energy to the external moisture sensor and transmits data to the outside from the building material.

According to the disclosure, the moisture sensor of the external sensor unit is not formed by the data communication unit, that is to say by an RFID tag for example, in this case, however, but rather is in the form of a separate component, for example a capacitive moisture sensor or a MEMS humidity sensor (MEMS=Microelectromechanical System) and is only read and is also supplied with energy via the data communication unit.

The energy provision unit of the external sensor unit may preferably also record and store sensor values autonomously, that is to say without an active energy supply from the outside, for a time by charging a transitional energy store, for example rechargeable batteries or capacitors provided in the external sensor unit.

In alternative embodiments, the external sensor unit can also intrinsically generate energy, for example via building vibrations or osmosis potentials of damp building materials.

The external sensor unit may also form an electrochemical element and may operate as a galvanic cell via the existing moisture in the material.

The external sensor unit advantageously has a known unique identifier programmed in, with the result that the installation location is determined once with the aid of an "electronic map" by means of a reader, for example the handheld measuring device, and the information relating to an operator.

The moisture sensor present in the external sensor unit is read for this purpose, its identifier is noted, the installation location is noted in the reader or in a computer, thus resulting in a map of all sensors installed in a room or building. As a follow-up, an operator can easily walk past the component, in which case the data can be automatically read and can be assigned to the installation location. Long-term measurements are therefore also possible, and the sensor position can also be combined with a floor plan or recorded there.

A measuring system, in particular a moisture measuring system, having at least one measuring device and having the at least one external sensor unit which is intended to record at least one further moisture characteristic value of the at least one building material is also proposed. The moisture measuring system preferably comprises a plurality of external sensor units which are preferably arranged at a distance from one another on or in the at least one building material. This makes it possible to advantageously record moisture measured values of at least one building material.

If the at least one external sensor unit is intended to be at least partially and preferably completely embedded in the at least one building material, it is possible to record the at least one further moisture characteristic value in an advantageously accurate manner. In particular, measurement errors can be largely eliminated by a measuring method which is carried out outside the at least one building material.

It is also proposed that the at least one external sensor unit has a further communication unit which is intended to emit the at least one signal. The one further communication unit is preferably intended to communicate with the communication unit of the measuring device, in particular in a bidirectional manner.

The further communication unit is preferably in the form of a further RFID communication unit. This makes it possible to achieve advantageous communication between the at least one external sensor unit and the measuring device and, in particular, advantageous transmission of the at least one further moisture characteristic value from the at least one external sensor unit to the measuring device.

The at least one external sensor unit preferably has an energy receiving unit for contactless energy supply.

In this context, an "energy receiving unit" is supposed to be understood as meaning, in particular, a unit which is intended to receive and/or preprocess electrical energy which is inductively and/or electromagnetically transmitted from an energy transmitting unit, in particular. This makes it possible to supply the at least one external sensor unit with electrical energy in an advantageously simple manner. The energy receiving unit is preferably integrally formed with the further energy supply unit. In particular, it is possible to dispense with an energy source inside the at least one external sensor unit, as a result of which a lifetime of the at least one external sensor unit can be advantageously extended.

One advantageous embodiment of a moisture measuring system has at least one, but preferably a plurality of, external sensor unit(s) and a measuring device which is in the form of a reader for reading the data from the external sensor unit and has at least one energy transmitting unit which is intended to contactlessly supply energy to the at least one external sensor unit. The reader itself then does not need to have an active moisture sensor, but rather can read only the moisture characteristic value from the assigned external sensor units.

The disclosure therefore proposes a device and a method in which a module in the form of an external sensor unit, in particular a watertight module, combines a moisture sensor with a communication component, for example an RFID tag. A moisture sensor with a low power consumption—for example a capacitively operating moisture sensor which measures the humidity and can measure the equilibrium moisture via a membrane with the building material—or a moisture sensor which is in contact with the building material either capacitively or resistively via electrodes and can therefore determine the local moisture is advantageously integrated in the watertight module, which is intended to remain in a building material, and is combined with a data reading and energy component. The module in the form of an external sensor unit advantageously has a communication component which is designed both for data communication and for the energy management of the moisture sensor. In this case, the moisture sensor and the data reading and energy component form different components. The moisture is not determined via the data reading and energy component, as is known from the prior art.

The external sensor device which is in the form of a watertight module, in particular, can advantageously measure the temperature in the building material, which temperature can then be used to determine the dew point in the masonry. For this purpose, the external sensor unit according to the disclosure also at least has a temperature sensor. A dew point in the material can therefore be determined on the basis of the material moisture and material temperature. (This is possible, for example, using the Glaser method or according to DIN 4108-3). If a plurality of sensors are introduced into the building material at different embedding depths, it is also advantageously possible to determine and externally read the location of the current dew point inside the building material, for example inside masonry.

In this case, the dew point can be calculated by the external sensor unit itself and the latter can hold, store, log and possibly output the characteristic values for moisture, temperature and dew point. Alternatively, an external apparatus, for example a reader or else the measuring device, can read the temperature and humidity and can calculate the dew point therefrom.

It is likewise possible to read the material temperature via the external sensor unit and to then determine a dew point on the surface of the building material together with a measured value for the air humidity. A dew point on the surface of the structure can then be determined using an external reader which reads the sensor data from the external sensor unit—together with the air humidity which is likewise measured.

In the case of a temperature dependence of the moisture sensor in the external sensor unit, a deviation/drift of the moisture sensor which possibly occurs can be advantageously compensated for by means of the measured temperature value.

The module is concomitantly introduced into the building material—for example encased in concrete—when producing the structure and can then be supplied with energy and read from "outside".

The measuring device according to the disclosure is not supposed to be restricted in this case to the use and embodiment described above. In particular, the measuring device according to the disclosure can have a number differing from a number of individual elements, components and units mentioned herein for the purpose of complying with a method of operation described herein.

BRIEF DESCRIPTION OF THE DRAWINGS

Further advantages emerge from the following description of the drawing. The drawing illustrates an exemplary embodiment of the disclosure. The drawing, the description and the claims contain numerous features in combination. A person skilled in the art will also expediently consider the features individually and will combine them to form useful further combinations.

In the drawing:

FIG. 1 shows a schematic illustration of a moisture measuring system having a measuring device, which has an integrated sensor unit, and an external sensor unit embedded in a building material.

DETAILED DESCRIPTION

FIG. 1 shows a schematic illustration of a moisture measuring system 30 having a measuring device 10 and an external sensor unit 18. The measuring device 10 is in the form of a moisture measuring device 32. The measuring device 10 is preferably in the form of a handheld apparatus 34. The measuring device 10 is intended, in particular, to determine a material and/or building moisture of a building material 14, for example of a wall and/or a floor of a building or a structure.

For this purpose, the measuring device 10 has an integrated sensor unit 12 which is intended to record a moisture characteristic value of the building material 14, by means of which a water content of the building material 14 can be inferred. In this case, the integrated sensor unit 12 is in the form of a capacitive sensor unit 36, for example. The sensor unit has three electrodes 38. In order to record the moisture characteristic value, the electrodes 38 of the integrated sensor unit 12 are brought into contact with a surface 40 of the building material 14. A proportion of water inside the building material 14, in particular, can be inferred by determining a material permittivity using an AC voltage between the electrodes 38, with a known dielectric constant of the building material 14 in the dry state. Alternatively and/or additionally, it is conceivable for a sensor unit to have at least one sensor system which is intended to record a moisture characteristic value of a building material radiometrically and/or resistively and/or using a microwave/radar method and/or using a one-sided access NMR method, for example. The methods which have been mentioned and are known to a person skilled in the art shall not be discussed here in detail. Furthermore, the list of methods should not be considered to be conclusive and it is likewise conceivable to use further methods which appear to be suitable to a person skilled in the art. In alternative embodiments, the measuring device 10 may be in the form only of a reader, which itself does not have an integrated sensor unit, and may be used to read one or more external sensor units 18 integrated in a building material.

It is particularly advantageous if the external sensor device 18 can also measure and possibly log the temperature. For this purpose, the external sensor device 18 may have at least one temperature sensor in advantageous embodiments.

A dew point in the material 14 itself can thus be determined using the material moisture and the material temperature. If a plurality of external sensor devices are introduced into the building material 14 at different embedding depths, the location of the current dew point inside the building material 14, for example masonry, can also be advantageously determined.

The measuring device 10 also has a communication unit 16 which is intended to receive a signal from an external sensor unit 18 of the moisture measuring system 30. The communication unit 16 is preferably in the form of an RFID reading unit 52.

The external sensor unit 18 is completely embedded in the building material 14, but may also be only partially embedded in the building material 14 in other applications. In this case, the external sensor unit 18 comprises, by way of example, two sensors 42, 44 which are each intended to record a moisture characteristic value of the building material 14. However, it is likewise conceivable to use only one sensor 42 or 44 and/or only one sensor type. One of the sensors 42 is in the form of a capacitive moisture sensor 46 for recording an air humidity. The sensor 42 is in contact with the building material 14 via an air-permeable but water-impermeable membrane 48, as a result of which it is possible to record an equilibrium moisture which provides information on a water content of the building material 14. The second sensor 44 has electrodes 50 which are in contact with the building material 14. The electrodes 50 can be used, for example, to capacitively and/or resistively record a material permittivity of the building material 14 which provides information on a water content of the building material 14. Since the external sensor unit 18 is directly embedded in the building material 14, a moisture characteristic value of the building material 14 can be exactly recorded and a water content of the building material 14 can therefore be precisely determined. The external sensor unit 18 may additionally have a temperature sensor which is not illustrated here. Recorded temperature values can be used, in combination with the moisture characteristic value, to calculate a dew point. Furthermore, a possible temperature drift of the sensors 42 can be compensated for.

In order to transmit a signal, which comprises the moisture characteristic values recorded by the sensors 42, 44 as useful data, from the external sensor unit 18 to the measuring device 10, the external sensor unit 18 has a further communication unit 26. The further communication unit 26 is preferably in the form of an RFID transponder 54, in particular a passive RFID transponder. Moisture characteristic values recorded by the external sensor unit 18 can be wirelessly retrieved from the external sensor unit 18 using the communication unit 26 of the measuring device 10 and are wirelessly transmitted from the further communication unit 26 of the external sensor unit 18 to the communication unit 16 of the measuring device 10.

Both the communication unit 16 of the measuring device and the further communication unit 26 of the external sensor unit 18 have a processing unit 56, 58 intended to buffer data and/or to process signals, for example.

The communication unit 16 is also used as an energy transmitting unit 24 which is intended to contactlessly supply the external sensor unit 18 with electrical energy.

The electrical energy is received by the further communication unit 26 of the external sensor unit 18, which is used as an energy receiving unit 28. This component of the external sensor unit 18 (for example an RFID tag) therefore advantageously both supplies energy to the moisture sensor 42 or 44 and transmits the determined sensor data to the outside to the measuring device. As a result, the moisture sensor 42 or 44 of the external sensor unit 18 does not have to have its own energy supply and can measure directly inside the building material in a non-destructive manner since it can be wirelessly read.

The energy transmitting unit 24 and the energy receiving unit 28 have a buffer store 60, for example a capacitor, for temporarily buffering electrical energy. Both signal transmission and energy transmission is carried out via an antenna 62, 64 of the communication units 16, 26.

The moisture characteristic values received from the integrated sensor unit 12 of the measuring device 10 and the further moisture characteristic values recorded by the external sensor unit 18 and received by the communication unit 16 of the measuring device 10 are offset against one another by a computing unit 20 of the measuring device 10. During this offsetting, a compensation characteristic variable is determined, which compensation characteristic variable reflects a difference between the exact moisture characteristic values from the external sensor unit 18 and the moisture characteristic values from the integrated sensor unit 12 which have a measurement inaccuracy.

A measurement inaccuracy of the integrated sensor unit 12 can be reliably compensated for with the aid of the compensation characteristic variable determined.

In order to output information to an operator, the measuring device 10 has a display unit 66 which can be used to output information relating to a water content of the building material 14. The measuring device 10 also has an interface 22 which can be used to transmit data in a wireless and/or wired manner from the measuring device 10 to external data processing apparatuses (not illustrated here), for example PCs, laptops and/or tablet PCs.

If the moisture measuring system 30 has a plurality of external sensor units 18 which are embedded in the building material 14 in a distributed manner, they can be read using the measuring device 10, as a result of which exact moisture characteristic values of the building material 14 can be recorded. If the building material 14 is sufficiently covered with a plurality of external sensor units 18, it is possible to dispense with use of the integrated sensor unit 12 in this case.

If the moisture measuring system 30 has only one external sensor unit 18, it can be read using the measuring device 10 in order to obtain an exact moisture characteristic value for the building material 14 at the installation location of the external sensor unit 18. A moisture characteristic value at a surface 40 of the building material 14 in the region of the external sensor unit 18 is then likewise recorded using the integrated sensor unit 12. The computing unit 20 determines a compensation characteristic variable on the basis of the recorded moisture characteristic values. If the building material 14 remains the same, moisture characteristic values which are recorded at another location using the integrated sensor unit 12 can now be corrected using the compensation characteristic variable. This allows moisture characteristic values to be exactly recorded using the integrated sensor unit 12.

The invention claimed is:

1. A handheld measuring device, comprising:
   an integrated sensor unit configured to record at least one moisture characteristic value of at least one building material; and
   a communication unit configured to receive at least one signal from at least one external sensor unit that is at least partially embedded in the at least one building material,
   wherein the at least one signal has at least one further moisture characteristic value of the at least one building material sensed by the at least one external sensor unit, and
   further comprising a computing unit configured to offset the at least one moisture characteristic value with respect to the at least one further moisture characteristic value.

2. The handheld measuring device as claimed in claim 1, wherein the communication unit is configured to wirelessly receive the at least one signal.

3. The handheld measuring device as claimed in claim 2, wherein the computing unit is further configured to determine at least one compensation characteristic variable from the at least one moisture characteristic value and the at least one further moisture characteristic value.

4. The handheld measuring device as claimed in claim 1, further comprising:
   at least one interface configured to transmit data to at least one external data processing unit.

5. The handheld measuring device as claimed in claim 1, further comprising:
   an energy transmitting unit configured to contactlessly supply energy to the at least one external sensor unit.

6. The measuring device as claimed in claim 1, wherein the handheld measuring device is a moisture measuring device.

7. A moisture measuring system, comprising:
   at least one handheld measuring device having:
      an integrated sensor unit configured to record at least one moisture characteristic value of at least one building material;
      a communication unit configured to wirelessly receive at least one signal from at least one external sensor unit, the at least one signal including at least one further moisture characteristic value of the at least one building material; and a computing unit configured to offset the at least one moisture characteristic value against the at least one further moisture characteristic value with respect to each other; and the at least one external sensor unit having:
at least one sensor configured to detect the at least one further moisture characteristic value of the at least one building material,
wherein the external sensor unit is configured to be at least partially embedded in the at least one building material.

8. The moisture measuring system as claimed in claim 7, wherein the at least one external sensor unit is configured to be at least partially embedded in the at least one building material.

9. The moisture measuring system as claimed in claim 7, wherein the at least one external sensor unit has:
a further communication unit configured to emit the at least one signal.

10. The moisture measuring system as claimed in claim 7, wherein the at least one external sensor unit has:
an energy receiving unit configured to contactlessly supply energy.

* * * * *